US005843109A

United States Patent [19]
Mehta et al.

[11] Patent Number: 5,843,109
[45] Date of Patent: Dec. 1, 1998

[54] ULTRASONIC HANDPIECE WITH MULTIPLE PIEZOELECTRIC ELEMENTS AND HEAT DISSIPATOR

[75] Inventors: Pravin V. Mehta, Huntington Beach, Calif.; George Bromfield, Salt Lake City, Utah

[73] Assignee: Allergan, Waco, Tex.

[21] Appl. No.: 654,837

[22] Filed: May 29, 1996

[51] Int. Cl.⁶ .................................................. A61B 17/32
[52] U.S. Cl. ........................... 606/169; 606/170; 604/22
[58] Field of Search ...................................... 606/169, 170, 606/167, 171, 185, 189; 604/22, 35, 272, 36, 43, 44, 156, 264, 266, 268, 274

[56] References Cited

U.S. PATENT DOCUMENTS

| | | | |
|---|---|---|---|
| 3,689,783 | 9/1972 | Williams | 310/8.3 |
| 3,694,675 | 9/1972 | Loveday | 310/8.9 |
| 3,805,787 | 4/1974 | Banko | 128/276 |
| 4,032,803 | 6/1997 | Durk et al. | 310/8.1 |
| 4,169,984 | 10/1979 | Parisi et al. | 606/169 |
| 4,838,853 | 6/1989 | Parisi | 606/169 |
| 4,979,952 | 12/1990 | Kubota et al. | 606/169 |
| 5,331,951 | 7/1994 | Kepley | 601/4 |
| 5,370,602 | 12/1994 | Kepley | 601/2 |
| 5,388,569 | 2/1995 | Kepley | 601/2 |
| 5,413,556 | 5/1995 | Whittingham | 604/22 |
| 5,562,610 | 10/1996 | Brumbach | 606/169 |
| 5,649,935 | 7/1997 | Kremer et al. | 606/169 |

FOREIGN PATENT DOCUMENTS

| | | |
|---|---|---|
| 0376562 | 7/1990 | European Pat. Off. . |
| 2249419 | 5/1992 | United Kingdom . |

*Primary Examiner*—Michael Powell Buiz
*Assistant Examiner*—Daphna Shai
*Attorney, Agent, or Firm*—Walter A. Hackler

[57] ABSTRACT

Handpiece apparatus is provided for disruption and removal of tissue, tumors, bone, cartilage, calculi or the like which includes an arrangement of piezoelectric crystals and a heat sink in order to control crystal temperature despite interruption of cooling irrigation flow through the handpiece.

20 Claims, 1 Drawing Sheet

ULTRASONIC HANDPIECE WITH MULTIPLE PIEZOELECTRIC ELEMENTS AND HEAT DISSIPATOR

The present invention generally relates to surgical instruments, and more particularly, is directed to a handpiece for selective removal of unwanted material in an animal body such as, for example, unwanted tissue, tumors, cartilage, bone, calculi or the like.

Ultrasound has found many medical/surgical applications for the removal of tissue, such as in phacoemulsification, bone and cartilage repair and in lithotripsy, the removal of calculi. All of these procedures involve the application of appropriate ultrasound of sufficient energy to emulsify, fragment or disrupt the selected tissue, cartilage, bone or calculi. In many operations the disrupted material is aspirated from the site by a handpiece which also supplies the ultrasonic energy.

As a specific example, phacoemulsification involves the fragmentation of lens tissue as is performed, for example, in cataract surgery. A transducer such as a piezoelectric crystal, converts an electrical signal into ultrasonic energy generally in the range of 20 to 100 KHz.

The ultrasonic energy generated by the crystal is coupled to a horn and a needle to radiate the ultrasonic energy into eye tissue for fragmentation or phacoemulsification thereof.

After the cataratic tissue is fragmented, it is removed from the eye by aspiration of irrigation fluid provided for maintaining intraocular pressure and for flushing of fragmented tissue. The aspiration of fluid is commonly conducted through the ultrasonic needle itself, which is hollow.

The flow of fluid through the needle and horn provides a means for cooling the piezoelectric crystals which generate heat as well as the ultrasonic energy. Unfortunately, the efficiency of a piezoelectric crystal in converting electrical signals to ultrasonic energy is temperature dependent. That is, overheating of piezoelectric crystals causes the significant decrease in their ultrasonic output. In fact, severe overheating may destroy the usefulness of the crystals in generating ultrasonic energy or cause permanent damage to the crystals.

In order to maintain the operating temperature of the piezoelectric crystals heretofore developed handpieces for phacoemulsification have used the hollow horn needle arrangement hereinabove described.

However problems arise during aspiration when disrupted tissue occlude or partially occlude the needle resulting in restricted flow through the needle. This restricted flow provides for less heat transfer from the piezoelectric crystals into the fluid flow and concomitant undesirable temperature rise of the crystals.

The present invention is directed to a handpiece for disruption and removal of unwanted material in an animal body. The handpiece includes a heat sink for maintaining piezoelectric crystal temperature during occluded and partial occluded fluid flow conditions through the handpiece.

SUMMARY OF THE INVENTION

Handpiece apparatus in accordance with the present invention useful for the disruption (ie, fragmentation, eroding, sloughing off and emulsification) and removal of unwanted material such as tissue, tumors, cartilage, bone, calculi or the like from an animal body such as a human, generally includes a housing and a horn having a needle which provides means for radiating ultrasonic energy into a body for emulsifying or fragmenting tissue, tumors, cartilage, bone calculi or the like. A lumen is provided, through the needle and horn, which provides a means for passing aspiration fluid therethrough along with the fragmented material and, importantly, for cooling of the horn during fluid flow therethrough.

Piezoelectric elements, which are disposed in thermal communication with the horn, are provided for generating ultrasonic energy into the horn and a heat sink is provided and disposed in thermal communication with the horn and the piezoelectric element for providing transient heat absorption from the piezoelectric element during stoppage and restricted fluid flow through the lumen and horn. The piezoelectric crystals may be axially aligned along a longitudinal axis of the handpiece.

Additionally, the heat sink provides a means for transferring absorbed heat to the horn and the fluid during unrestricted fluid flow through the lumen.

In this manner, the heat sink means protects the piezoelectric element from undesirable heating during periods of low fluid flow through the horn thus stabilizing the efficiency of the piezoelectric elements during their continued operation. More particularly, the horn includes a body portion which passes through a plurality of piezoelectric crystals each having a torus shape. The heat sink may also comprise a high Q metallic material having a torus shape.

Importantly, the heat sink is disposed between at least two of the plurality of piezoelectric elements, or crystals, and if four piezoelectric crystals are utilized, the heat sink is preferably disposed between adjacent pairs of the plurality of piezoelectric crystals.

Still more particularly, the horn body portion may include a center portion and a rear portion with the rear portion passing through the plurality of piezoelectric crystals. In this embodiment, the horn rear portion has a diameter smaller than a diameter of the center portion and each of the plurality of the piezoelectric crystals have a torus shape with an inside diameter approximately equal to the rear portion diameter and an outside diameter approximately equal to the center portion diameter. In this manner a streamline configuration of the horn piezoelectric crystals may be maintained for easy accommodation within the housing.

While the present invention is directed to a handpiece incorporating the particular configuration of piezoelectric elements and heat sink, it is to be appreciated that the invention also is directed to an improvement for a handpiece which utilizes piezoelectric elements for generating ultrasonic energy. In addition the present invention is particularly suited for use in phacoemulsification, ie the selective removal of eye tissue as such in cataract removal.

BRIEF DESCRIPTION OF THE DRAWINGS

The present invention can be more readily understood by consideration of the following detailed description, particularly in conjunction with the accompanying drawings in which.

DETAILED DESCRIPTION OF THE INVENTION

Figure 1:
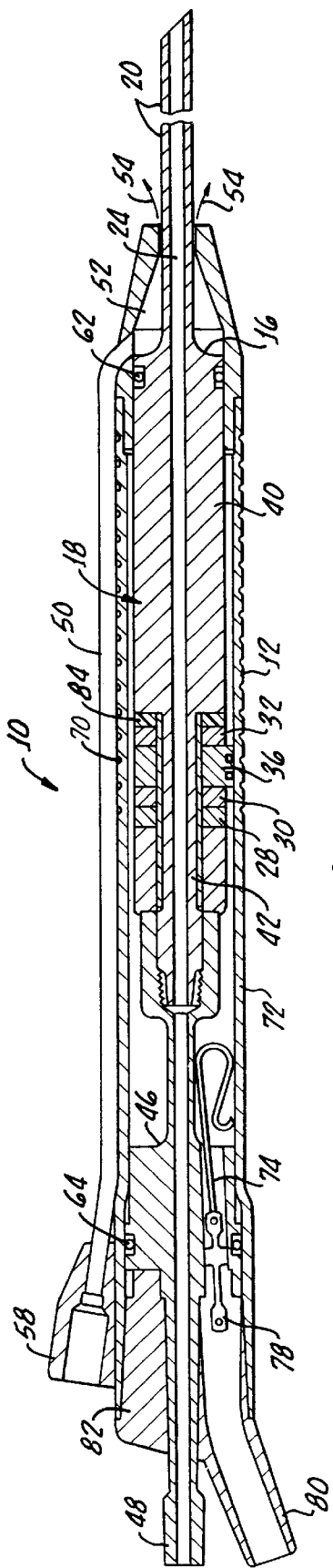
FIG. 1 is a cross-sectional view of an embodiment of the present invention utilizing three piezoelectric crystals and a heat sink disposed between and around a radiating ultrasonic horns.

Turning now to FIG. 1 there is shown a handpiece apparatus 10 in accordance with the present invention showing a housing 12 which is formed from any suitable material disposed around a horn 16 having a body portion 18 and a needle 20 which provides means for radiating ultrasonic energy into an eye, not shown, for fragmenting eye tissue.

A lumen 24 is established through the needle 20 and horn 16 which provides a means for aspiration fluid in fragmented eye tissue and for cooling of the horn and piezoelectric crystals 28, 30, 32 as hereinafter described in greater detail. While three piezoelectric crystals, or elements, are shown in FIG. 1, it is to be appreciated that a greater or smaller number of elements may be utilized in combination with a heat sink 36 as hereinafter to be described in greater detail.

It should be appreciated that the piezoelectric crystals, or elements, may be of any conventional suitable design heretofore used in phacoemulsification handpieces. The horn 16 may be formed from any suitable material such as, for example, titanium or stainless steel and the body portion 18 may include a center portion 40 and a rear portion 42 as will be discussed hereinafter in greater detail in combination with the piezoelectric crystals 28, 30, 32.

The lumen 24 extends through the needle 20 and horn 16 as well as through a rear body mass 46 which includes a coupling 48 for interconnection with a power supply, not shown. It should be appreciated that the apparatus shown in FIG. 1 is particularly suitable for use in phacoemulsification of eye tissue and accordingly, the size of the housing 12, horn 16, needle 20 and other components are appropriately sized and arranged. Other handpieces made in accordance with the present invention will have specific features and be of appropriate size for the disruption of other types of tissue, tumors, bone, cartilage and/or calculi.

Mounted exterior to the housing 12 is an irrigation channel 50 which communicates to a chamber 52 established around the needle 20 for providing irrigation fluid therepast as indicated by arrows 54. A balanced salt solution is typically utilized as the irrigation fluid and is provided to the channel 50 through an irrigation input coupling 58 from an exterior source, not shown.

O-rings 62, 64 provide a means for sealing the horn and rim mass within the housing 12 in the conventional manner.

Electrical connection to the piezoelectric crystals 28, 30, 32 is made through terminals 70, 72 and are connected by wire 72 to a connector 78 to which a power source (not shown) is connected through a sleeve 80 in a solid sealing material 82 deposited against the body mass 46.

As shown in FIG. 1, the piezoelectric crystals 28, 30, 32, as well as the heat sink 36 have a torus, or washer shape and are disposed with two piezoelectric crystals 28 and 30 in a abutting relationship and the heat sink 36 sandwiched between the pair of abutting piezoelectric crystals 28, 30 and the third piezoelectric crystal 32. An insulating washer 84 provides electrical and heat insulation between the piezoelectric crystal 32 and the center portion 40 of the horn body portion 18.

Figure 2:
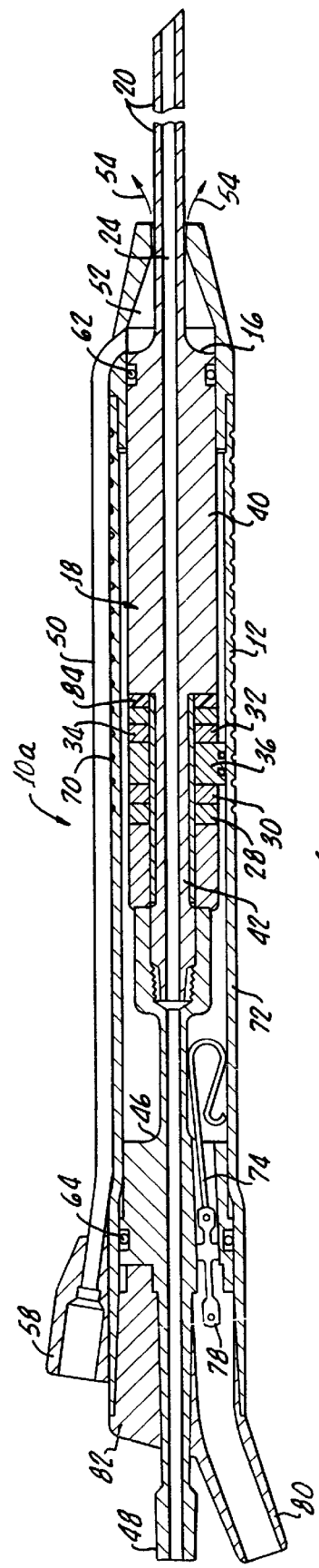
FIG. 2 is a cross sectional view of another embodiment of the present invention utilizing four piezoelectric crystals with a heat sink disposed between adjacent pairs of the piezoelectric crystals.

FIG. 2 shows an alternative embodiment 10a of the present invention having four piezoelectric crystals 28, 30; 32, 34 with the heat sink 36 disposed between adjacent pairs of the piezoelectric crystals 28, 30; 32, 34. It should be appreciated that common reference characters shown in FIGS. 1 and 2 represent identical or substantially equivalent structure.

As shown, the rear portion 42 has a diameter of approximately equal to the inside diameter the piezoelectric crystals 28, 30, 32, heat sink 36 and washer 84 with an outside diameter of these elements approximately equal to the center portion 18 of the horn 16. This configuration enables a smooth outer contour in order that the conforming housing 12 provides a uniform exterior cylindrical surface for the grasping of the handpiece apparatus 10 by physician.

It is preferable that all of the piezoelectric crystals 28, 30, 32 as well as the heat sink 36 and washer 84 be snugly fit as shown in FIG. 1 in order to maximize heat transfer therebetween.

The heat sink 36 is preferably made from a high Q metallic material, such as, aluminum.

In operation when unrestricted flow of fluid occurs through the lumen 28 during aspiration, cooling is provided for the piezoelectric crystals 28, 30, 32 through the rear portion 42 of the horn body portion 18. The smaller diameter of this rear portion 42 provides for a shorter heat path from the lumen to the piezoelectric crystals 28, 30, 32 to enhance heat transfer from the piezoelectric crystals 28, 30, 32 to the irrigation fluid passing through lumen 24.

Upon partial or total occlusion of the lumen by fragmented eye tissue during aspiration, not shown, significant reduction of heat transfer from the crystals 28, 30, 32 may occur. This may result in overheating of the crystals and serious reduction in their efficiency which is prevented, in accordance with the present invention, by the heat sink 36. This protection of overheating is accomplished through the use of the heat sink 36 since it provides for transient heat absorption of the excess heat generated by the crystals 28, 30, 32 during such stoppage or restricted fluid flow through the lumen.

To enhance this transient absorption of heat, the heat sink 36 is preferably disposed between the crystals 28, 30, 32. It should be appreciated that any number of crystals may be provided along with the plurality of heat sinks, not shown, as long as the piezoelectric crystals and heat sinks are arranged for providing intimate contact therebetween to enable and promote transient heat transfer therebetween.

The heat sink also functions to transfer the absorbed heat to the horn and fluid passing through the lumen upon resumed unrestricted fluid flow through the lumen 24. Thus, the heat sink acts as heat modulator, that is it functions to maintain the crystal temperature despite the rate of fluid flow to the lumen 24 and horn 16.

Although there has been hereinabove described a particular arrangement of handpiece apparatus in accordance with the present invention for the purpose of illustrating the manner in which the invention may be used to its advantage, it should be appreciated that the invention is not limited thereto. Accordingly, any and all modifications, variations or equivalent arrangements which may occur to those skilled in the art, should be considered to be within the scope of the present invention as defined in the appended claims.

What is claimed is:

1. Handpiece apparatus for disruption and removal of unwanted material from an animal body, said handpiece apparatus comprising:

a housing;

a plurality of piezoelectric crystals dispersed within said housing;

a horn having a body portion passing through the plurality of piezoelectric crystals and needle means for radiating ultrasonic energy into an animal body for disrupting unwanted material, said horn including lumen means, passing through the needle means and body portion, for aspiration of fluid and disrupted material and for cooling of the plurality of piezoelectric crystals during flow of the fluid therethrough; and high Q heat sink means, disposed between at least two of said plurality of piezoelectric crystals, for providing transient heat absorption from said plurality of piezoelectric crystals during stoppage or restricted fluid flow through said lumen means and for transferring absorbed heat to the horn and fluid during unrestricted fluid flow through said lumen means.

2. Handpiece apparatus for phacoemulsification of eye tissue, said handpiece apparatus comprising:

a housing;

a plurality of piezoelectric crystals dispersed within said housing;

a horn having a body portion passing through the plurality of piezoelectric crystals and needle means for radiating ultrasonic energy into an eye for fragmenting eye tissue, said horn including lumen means, passing through the needle means and horn portion, for aspiration of fluid and fragmented eye tissue and for cooling of the plurality of piezoelectric crystals during flow of the fluid therethrough; and high Q heat sink means, disposed between at least two of said plurality of piezoelectric crystals, for providing transient heat absorption from said plurality of piezoelectric crystals during stoppage or restricted fluid flow through said lumen means and for transferring absorbed heat to the horn and fluid during unrestricted fluid flow through said lumen means.

3. The handpiece apparatus according to claim 2 wherein said plurality of piezoelectric crystals comprises three piezoelectric crystals having a torus shape and said heat sink means comprises a high Q metallic material having a torus shape.

4. The handpiece apparatus according to claim 2 wherein said plurality of piezoelectric crystals comprises four piezoelectric crystals and said heat sink means is disposed between adjacent pairs of said four piezoelectric crystals.

5. The handpiece apparatus according to claim 4 wherein said heat sink means and each of said plurality of piezoelectric crystals have a torus shape.

6. The handpiece of apparatus according to claim 2 wherein the horn body portion includes a center portion and a rear portion with said rear portion passing through said plurality of piezoelectric crystals.

7. The handpiece apparatus according to claim 6 said horn rear portion has a diameter smaller than a diameter of said center portion, each of said plurality of piezoelectric crystals have a torus shape with an inside diameter approximately equal to the rear portion diameter and an outside diameter approximately equal to the center portion diameter.

8. In a handpiece for phacoemulsification of eye tissue having a horn and a needle for radiating ultrasonic energy into the eye tissue with a lumen passing through the needle and horn for aspiration of fluid and fragmented eye tissue and for cooling of the horn during fluid flow therethrough, the improvement comprising:

piezoelectric means, dispersed in thermal communication with said horn, for generating ultrasonic energy into said horn, said piezoelectric means including a plurality of piezoelectric crystals; and high Q heat sink means, disposed between at least two of said plurality of piezoelectric crystals, for providing transient heat absorption from said plurality of piezoelectric crystals during stoppage and restricted fluid flow through said lumen and horn or for transfer of absorbed heat to said horn and fluid during unrestricted fluid flow through said lumen and horn.

9. The handpiece apparatus according to claim 8 wherein said plurality of piezoelectric crystals comprises three piezoelectric crystals having a torus shape and said heat sink means comprises a high Q metallic material having a torus shape.

10. The handpiece apparatus according to claim 8 wherein said plurality of piezoelectric crystals comprises four piezoelectric crystals and said heat sink means is disposed between adjacent pairs of said four piezoelectric crystals.

11. The handpiece apparatus according to claim 10 wherein said heat sink means and each of said plurality of piezoelectric crystals have a torus shape.

12. The handpiece of apparatus according to claim 8 wherein the horn comprises a center portion and a rear portion with said rear portion passing through said plurality of piezoelectric crystals.

13. The handpiece apparatus according to claim 12 said horn rear portion has a diameter smaller than a diameter of said center portion, each of said plurality of piezoelectric crystals have a torus shape with an inside diameter approximately equal to the rear portion diameter and an outside diameter approximately equal to the center portion diameter.

14. Handpiece apparatus for phacoemulsification of eye tissue, said handpiece apparatus comprising:

a housing;

a horn having needle means for radiating ultrasonic energy into an eye for fragmenting eye tissue and lumen means, passing through the horn and needle means, for aspiration of fluid and fragmented eye tissue and for cooling of the horn during fluid flow therethrough;

piezoelectric means, disposed in thermal communication with said horn, for generating ultrasonic energy into said horn; and high Q heat sink means, dispersed in thermal communication with said horn and piezoelectric means, for providing transient heat absorption from said piezoelectric means during stoppage or restricted fluid flow through said lumen means and horn and for transferring absorbed heat to said horn and fluid flow through said lumen means.

15. The handpiece apparatus according to claim 14 wherein said piezoelectric means comprises a plurality to piezoelectric crystals arranged axially along a longitudinal axis of the handpiece apparatus.

16. The handpiece apparatus according to claim 15 wherein said plurality of piezoelectric crystals comprises three piezoelectric crystals having a torus shape and said heat sink means comprises a high Q metallic material having a torus shape.

17. The handpiece apparatus according to claim 15 wherein said plurality of piezoelectric crystals comprises four piezoelectric crystals and said heat sink means is disposed between adjacent pairs of said four piezoelectric crystals.

18. The handpiece apparatus according to claim 17 wherein said heat sink means and each of said plurality of piezoelectric crystals have a torus shape.

19. The handpiece of apparatus according to claim 15 wherein the horn comprises a center portion and a rear portion with said rear portion passing through said plurality of piezoelectric crystals.

20. The handpiece apparatus according to claim 19 said horn rear portion has a diameter smaller than a diameter of said center portion, each of said plurality of piezoelectric crystals have a torus shape with an inside diameter approximately equal to the rear portion diameter and an outside diameter approximately equal to the center portion diameter.

* * * * *